United States Patent

Mayer et al.

[11] Patent Number: 4,617,151
[45] Date of Patent: Oct. 14, 1986

[54] 2- OR 2,3-SUBSTITUTED 5,6,11,12-TETRATHIOTETRACENE AND 5,6,11,12-TETRASELENOTETRACENE

[75] Inventors: Carl W. Mayer, Riehen; Vratislav Kvita, Reinach; Josef Pfeifer, Therwil, all of Switzerland

[73] Assignee: Ciba-Geigy Corporation, Ardsley, N.Y.

[21] Appl. No.: 712,291

[22] Filed: Mar. 15, 1985

[30] Foreign Application Priority Data

Mar. 23, 1984 [CH] Switzerland ................ 1468/84

[51] Int. Cl.$^4$ ............... C07D 517/02; C07D 517/12
[52] U.S. Cl. ................................ 540/1; 430/70; 430/71; 430/72; 430/75; 430/83; 548/417; 549/31; 549/34; 549/35; 549/39; 549/234
[58] Field of Search ........... 260/239 R; 549/31, 34, 549/35, 39, 234; 548/417; 430/70, 71, 72, 75, 83

[56] References Cited

U.S. PATENT DOCUMENTS 4,465,752 8/1984 Sugiuchi et al. .............. 260/239 R
4,465,845 8/1984 Okamoto et al. .............. 260/239 R

FOREIGN PATENT DOCUMENTS 54109 6/1982 European Pat. Off. .
65243 11/1982 European Pat. Off. .

OTHER PUBLICATIONS

V. Kvita et al., Helv. Chim. Acta, 66, 2769 (1983).
C. Marschalk et al., Bull. Soc. Chim. France, 1948, 422.
F. B. Kaufman et al., Appl. Phys. Letters 36, 422 (1980).
Y. Tomkiewicz et al., Appl. Phys. Letters 40, 90 (1982).

Primary Examiner—Donald G. Daus
Assistant Examiner—Cecilia Shen
Attorney, Agent, or Firm—Luther A. R. Hall

[57] ABSTRACT 2- or 2,3-substituted 5,6,11,12-tetraseleneotetracene or -tetrathiotetracene of the formula

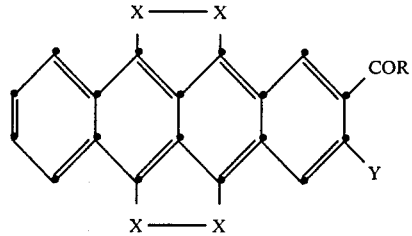

in which X is S or Se, R is alkoxy, hydroxyalkoxy, aryloxy, cycloalkoxy, aralkoxy, —OH, —NH$_2$, —Cl, —Br or substituted amino and Y is hydrogen or —COR. The compounds can be bonded as side groups to polymers. The polymers and the compounds combine with electron acceptors to form charge transfer complexes which can be used as electrically conductive layers.

3 Claims, No Drawings

2- OR 2,3-SUBSTITUTED 5,6,11,12-TETRATHIOTETRACENE AND 5,6,11,12-TETRASELENOTETRACENE

EP-A-0,065,243 discloses photoconductive compositions for electrophotographic recordings. A component of said composition are polymers based on acrylic acid and methacrylic acid which have each been esterified with 2-hydroxy-(alkyl)-5,6,11,12-tetrathiotetracene or 2-hydroxy(alkyl)-5,6,11,12-tetraselenotetracene.

The polymers are obtained by esterifying acrylic acid or methacrylic acid with 2-hydroxytetracene or 2-(hydroxyalkoxy)tetracene, polymerising the resulting esters and only then reacting the polymer with sulfur and selenium to introduce respectively the thio and selenium groups into the tetracene radical. It is necessary to employ this method of preparation because 2-hydroxytetracene is unstable under the reaction conditions employed for introducing sulfur and selenium bridges.

The subsequent introduction of the sulfur and selenium groups into the polymer is felt to be disadvantageous irsofar as it is impossible to obtain a complete reaction and it is difficult to obtain reproducible results. For that reason, it is desirable to have access to tetrathiotetracene or tetraselenotetracene having a functional group which can be used for preparing defined polymers.

The invention accordingly provides a 2- or 2,3-substituted 5,6,11,12-tetrathiotetracene and 5,6,11,12-tetraselenotetracene of the formula I

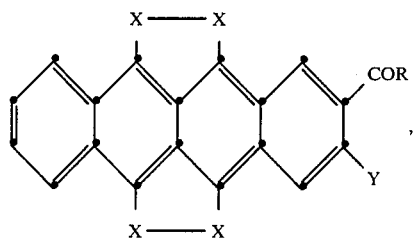

(I)

in which X is S or Se and and R is alkoxy having 1 to 12 C atoms, cycloakloxy having 5 to 16 C atoms, $\omega$-hydroxyalkoxy, having 2 to 12 C atoms, aryloxy having 6 to 16 C atoms, aralkoxy having 7 to 12 C atoms, —OH, —NH$_2$, —Cl, —Br or —NR$^1$R$^2$ in which R$^1$ is alkyl having 1 to 12 C atoms, cycloalkyl having 5 to 16 C atoms, $\omega$-hydroxyalkyl having 2 to 12 C atoms, aryl having 6 to 16 C atoms or aralkyl having 7 to 16 C atoms and R$^2$ is a hydrogen atom or independently is defined in the same way as R$^1$, and Y is a hydrogen atom or a —COR group or Y and R together are —CO—O— or —CO—NR$^2$.

An alkoxy R can be linear or branched and preferably contains 1 to 6 C atoms. Examples are methoxy, ethoxy, n-propoxy, n-butoxy, isobutoxy, hexoxy, octoxy, decoxy and dodecoxy. Preference is given to ethoxy and in particular methoxy.

A cycloalkoxy R preferably contains 5 or 6 ring carbon atoms. Examples are cyclopentoxy, cyclohexoxy and methylcyclohexoxy.

An $\omega$-hydroxyalkoxy R preferably contains 2 to 6 C atoms and can be linear or branched. Examples are 2-hydroxyethoxy, 2-hydroxypropoxy, 2,3-dihydroxypropoxy and 3-hydroxybutoxy.

An aryloxy and aralkoxy R is preferably derived from phenyl and benzyl respectively. Examples are phenoxy and benzyloxy.

Alkyls R$^1$ and R$^2$ can be linear or branched and preferably contain 1 to 6 C atoms. Examples are methyl, ethyl, n-propyl, i-propyl, n-butyl, pentyl and hexyl. Cycloalkyls R$^1$ and R$^2$ are preferably cyclopentyl or cyclohexyl. $\omega$-Hydroxyalkyls R$^1$ and R$^2$ have the same preferred definition as $\omega$-hydroxyalkyl R. Aryls R$^1$ and R$^2$ are preferably phenyl and aralkyls R$^1$ and R$^2$ are preferably benzyl. Preference is given to those —NR$^1$R$^2$ radicals in which R$^2$ is a hydrogen atom.

In a preferred embodiment, R in the formula I is methoxy, ethoxy, 2-hydroxyethoxy, 3-hydroxypropoxy, 4-hydroxybutoxy, 6-hydroxyhexoxy, —OH, —Cl, —NH$_2$, —NHCH$_3$, —NHC$_2$H$_5$ or NHCH$_2$CH$_2$OH. Y and R together are preferably —CO—O— or —CO—NR$^2$— with R$^2$ being H, —CH$_3$, C$_2$H$_5$ or —CH$_2$—CH$_2$OH.

The invention also provides a process for preparing tetracenes of the formula I which comprises reacting a compound of the formula II

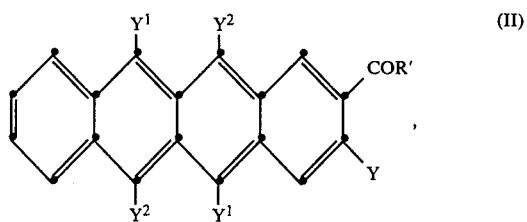

(II)

in which Y$^1$ is Cl and Y$^2$ is H or Y$^1$ is H and Y$^2$ is Cl, Y is —COR$^2$ or H and R' are the monovalent radical of an alcohol, at elevated temperature with sulfur or selenium, and, if desired, converting these carboxylic acid esters in a manner known per se into carboxylic acid derivatives of the formula I.

A monovalent radical of an alcohol, R' is preferably an alkoxy radical, in particular methoxy or ethoxy. The resulting carboxylic acid esters can be converted by known methods into carboxylic acid derivatives of the formula I. The free carboxylic acid is obtainable by hydrolysis and can be converted into the chlorides or bromides of the acid. The amides of the carboxylic acid are obtained by amidating the carboxylic acids or halides thereof or the carboxylic acid esters. Carboxylic acid esters can be obtained in a simple manner by transesterification. The anhydrides are obtainable from the dicarboxylic acids through loss of water following the use of dehydrating agents. The imides of the dicarboxylic acids can be prepared by reacting the dicarboxylic acid anhydrides or halides or esters with ammonia or secondary amines.

The reaction with sulfur or selenium is effected at elevated temperature, preferably at least 130° C. The reaction is advantageously carried out in halogenated aromatic hydrocarbons, in particular 1,2,4-trichlorobenzene.

The compound of the formula II can be prepared by the following multistage method:

First, a 1,2-substituted butadiene of the formula V

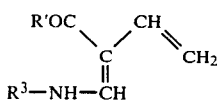

is prepared by known methods [cf. V. Kvita et al., Helv. Chim. Acta 66, 2769 (1983)] by reacting an aniline of the formula $R^3NH_2$ with coumaric acid ester and decarboxylating the resulting acid of the formula

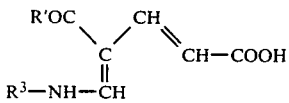

R' in the formula V is the monovalent radical of an alcohol, preferably alkoxy having 1 to 4 C atoms, in particular methoxy. $R^3$ in the formula V is the radical of an arylamine having a $pK_a$ value of at least 1.05. Preferred arylamines are phenylamines. Examples are aniline, toluidine and halogenated phenylamines, for example p-fluoroaniline and in particular p-chloroaniline.

The compound of the formula V is reacted in a Diels-Alder reaction, preferably at temperatures around 50° C. and in a polar solvent, for example dimethyl sulfoxide, with 1,4-anthraquinone to form, through elimination of $R^3NH_2$, 2-R'OC-5,12-naphthacenedihydroquinone of the formula

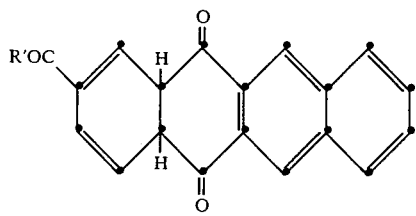

which undergoes rearrangement to the corresponding hydroquinone.

In the reaction medium used, this hydroquinone is unstable to air and undergoes spontaneous oxidation to 2-(R'OC)-5,12-naphthacenequinone of the formula IV a

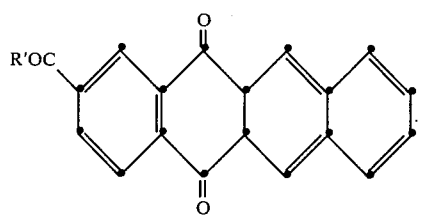

Anthraquinones of the formula IVb can be prepared as follows:

Commercially available aconitic acid ester of the formula

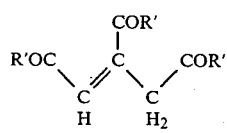

is reacted at temperatures of about 0° C. to 20° C. in an inert solvent, for example tetrahydrofuran, and in the presence of titanium tetrachloride and tetrachloromethane with ethyl formate to give a compound of the formula

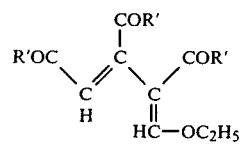

This compound is converted at elevated temperatures, for example 70° to 150° C., through the action of formic acid to the α-pyrone of the formula

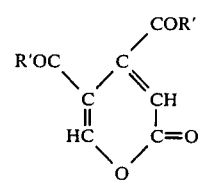

The Diels-Alder reaction at elevated temperatures, for example 100° to 200° C., under atmospheric or superatmospheric pressure with 1,4-anthraquinone leads, through decarboxylation, to 2,3-(R'OC)-5,12-naphthacenequinone of the formula IVb

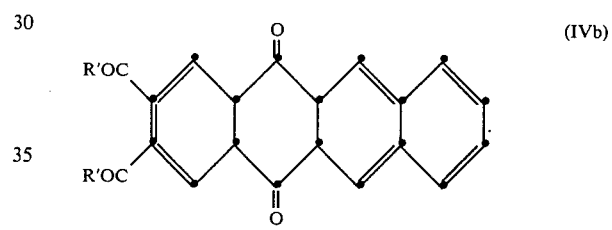

The quinones of the formulae IVa and IVb are reduced in a manner known per se to the 2- or 2,3-(R'OC)-tetracene of the formula III

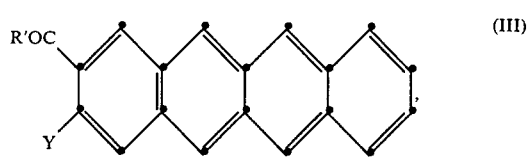

The reduction is effected in an acid reaction medium, for example acetic acid, with hydrogen in statu nascendi on zinc dust. Any 5,12-dihydrotetracene formed in the course of the reaction can be dehydrogenated with an oxidising agent, for example chloroanil, to give tetracene.

The tetracene of the formula III is chlorinated to 2 - or 2,3-(R'OC)-5,11- or 2- or 2,3-(R'OC)-6,12-dichlorotetracene of the formula II, for example with sulfuryl chloride [cf. Bull. Soc. Chim. France, 427 (1948)].

The compounds of the formula II, III, IVa and IVb are novel and are likewise provided by the present invention.

The compounds of the formula I are crystalline solids of black to blackish green colour. The compounds are thermally stable in the absence of air and can be subsequently incorporated in natural or synthetic polymers via one or both functional R'OC groups, this possibility constituting a method whereby polymers having a defined tetrathiotetracene or tetraselenotetracene group content can be prepared at will.

The present invention also provides polymers which contain groups of the formulae VIa, VIb or VIc

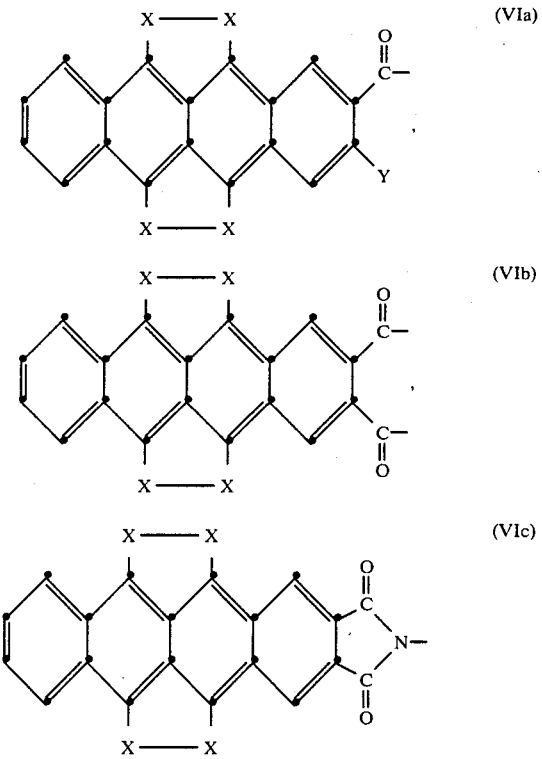

in which Y is H or a

$$-\overset{O}{\underset{\parallel}{C}}OR$$

group, as side groups and/or end groups and/or linking or crosslinking groups.

The polymers can have a mean molecular weight of $10^3$ to $10^6$, preferably $5 \times 10^3$ to $5 \times 10^5$. The polymers can be linear or crosslinked.

Suitable polymers have in their repeat structural elements terminal and/or lateral hydroxyl groups or amino groups or carboxyl groups. Examples thereof are epoxy resins, cellulose, polyvinyl alcohol, polyvinyl alcohols, which have been partially or completely esterified with hydroxyalkyl groups, homopolymers of maleic acid, maleic anhydride, acrylic acid and methacrylic acid whose carboxyl groups can contain $C_2$-$C_{12}$—, in particular $C_2$-$C_6$-hydroxyalkyl or aminoalkyl, and copolymers of these monomers with vinyl comonomers.

In a preferred embodiment, the polymers according to the invention contain repeat structural elements of the formula VII

in which $R^4$ is a direct bond or —$C_nH_{2n}O$— with n=2 to 12, preferably 2 to 6, and A is a radical of the formula VIa, or $R^4$ denotes —$C_nH_{2n}$— and A is a radical of the formula VIc.

The polymers can contain up to 80 mol %, preferably up to 50 mol %, and in particular up to 20 mol % of other structural elements of vinyl comonomers. Examples of such comonomers are: α-olefins, vinyl halides, for example vinyl bromide, vinyl chloride and vinyl fluoride, vinylidene, for example vinylidene chloride, nitriles, α,β-unsaturated acids, for example acrylonitrile or methacrylonitrile, α,β-unsaturated acids, their esters or halogen derivatives, for example acrylic acid, methacrylic acid, crotonic acid, maleic acid, methyl methacrylate, ethyl acrylate, propyl acrylate, butyl acrylate, octyl acrylate, 2-ethylhexyl acrylate, ethyl methacrylate, isopropyl methacrylate, dimethylaminoethyl methacrylate, diethylaminoethyl acrylate, glycidyl methacrylate, glycidyl acrylate or chloromethyl methacrylate, α,β-unsaturated carboxamides and their derivatives, for example acrylamide, methacrylamide, aromatic vinyl compounds, for example styrene, methylstyrene, vinyltoluene or α-chlorostyrene, vinyl ketones, for example methyl vinyl ketone, vinyl esters, for example vinyl acetate, heterocyclic vinyl compounds, for example vinylpyridine and vinylpyrrolidone, and vinyl ethers.

Other preferred polymers contain repeat structural elements of the formula VIIa or VIIb

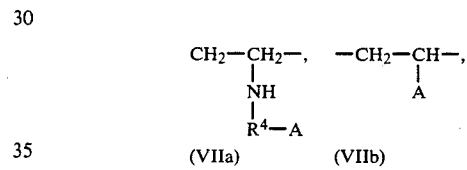

where, in the formula VIIa, $R^4$ is —$C_nH_{2n}O$— and A is a radical of the formula VIa, or $R^4$ is —$C_nH_{2n}$— and A is a radical of the formula VIc. In the formula VIIb, A is a radical of the formula VIc.

The homopolymers and copolymers according to the invention can be prepared by reacting the hydroxyl-, amino-, carboxyl- or carboxycarbonyl-containing polymers with ester-forming, amide-forming or imide-forming compounds of the formula I, i.e. with the esters, carboxylic acids, carboxylic anhydrides and carbonyl halides. The reaction is preferably carried out in solution and at elevated temperatures, for example at 50° to 200° C. The resulting polymers according to the invention can be isolated by precipitation with a nonsolvent or by evaporation of the solvent used.

Other preferred homopolymers and copolymers are derived from α,β-unsaturated carboxylic acids, for example from acrylic acid, methacrylic acid or maleic acid or maleic anhydride. The copolymers can include the abovementioned comonomers in the specified mixing ratios.

In a further preferred embodiment, the polymers according to the invention contain repeat structural elements of the formulae VIII and/or IX

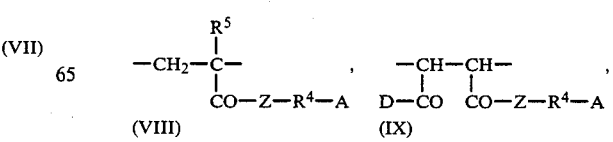

in which $R^5$ is H or $CH_3$, Z is —O— or —$NR^7$—, in which $R^7$ is H or alkyl having 1 to 4 C atoms; $R^4$ is —$C_nH_{2n}Z$— with n=2 to 12, A is a radical of the formula VIa and D is —OH or a —Z—$R^4$—A— group; or $R^4$ is —$C_nH_{2n}$— and A is a radical of the formula VIc. Z is preferably —O—, $R^4$ preferably contains 2 to 6 C atoms, and $R^7$ is preferably $CH_3$ and in particular H. Examples of $R^4$ are —$(CH_2)_6$—O—, —$(CH_2)_5$—O—, —$(CH_2)_3$—O—, —$CH_2CHCH_3$—O—, —$CH_2CHOHCH_2$—O— and in particular —$CH_2CH_2O$—, ethylene, 1,2- or 1,3-propylene, 1,2-, 1,3- or 1,4-butylene, 1,5-pentylene and 1,6-hexylene. The radical D in the formula IX is preferably —OH.

Polymers with structural elements of the formulae VIII and/or IX can be prepared by known methods. For instance, monomers of the formula I having hydroxyl groups or amino groups in the radical R can be converted into respectively the esters and amides of acrylic acid or methacrylic acid, for example with the corresponding acid halides. The reaction of such monomers with maleic anhydride leads to the half-esters and half-amides respectively. These esters can be polymerised in conventional manner either alone or together with other comonomers. It is also possible to react homopolymers and copolymers of acrylic acid, methacrylic acid and/or maleic acid or their ester- or amide-forming derivatives (for example esters, hydroxyalkyl esters, anhydrides and amides) with ester- or amide-forming derivatives of compounds of the formula I, and the polymers can be isolated by means of known methods.

It is thus possible to use the compounds according to the invention as starting materials for the preparation of polymers containing a defined amount of radicals of the formulae VIa to VIc. The polymers are film-forming and are powerful electron donors. As donors these polymers react with electron acceptors to give charge transfer complexes of high electric conductivity. An example of a suitable electron acceptor is iodine. The polymers according to the invention can also be used for coating various substrates, such as metals or plastic materials, and these materials be used as electrochromic electrodes [cf. Appl. Phys. Lett. 36(6), 422 (1980)].

The polymers according to the invention can also be used as electron beam resist [cf. Appl. Phys. Lett. 40(1), 90 (1982)].

The polymers according to the invention can also be used for photoconductive compositions. The present invention also provides such photoconductive compositions as contain (a) a polymer according to the invention together with an electron acceptor and/or sensitiser. The electron acceptors are preferably used in an amount of 0.1 to 1 mole per mole of polymer (a), and the sensitisers preferably in an amount of 0.1 to 40, preferably 1 to 20, % by weight, based on said polymer (a).

Examples of suitable electron acceptors are iodine, bromine, metal halides (Lewis acids), such as $SbF_5$ or $BF_3$, quinones, aromatic nitro compounds and tetracyanoethylene, which are described, for example, in EP-A-0,065,243. Said publication also describes suitable sensitisers, for example dyes such as methylene blue, chemical sensitisers such as maleic acid, p-nitrophenol and tetrachlorobisphenol A.

The compositions according to the invention can be prepared by dissolving and mixing the components (a) and (b). The preparation can be carried out in the presence or absence of a binder. Examples of suitable solvents are benzene, trichlorobenzene, nitrobenzene, acetone, methanol, chloroform, tetrahydrofuran, dimethylacetamide, dimethyl sulfoxide and N-methylpyrrolidone.

The solutions can be used for coating substrates which can be used as electrophotographic recording material in known methods (cf. for example EP-A-0,065,243).

The novel compounds and polymers can also be used for preparing video recording materials (cf. EP-A-0,054,109).

The novel compounds of the formula I can also be used directly for preparing electrically conductive charge transfer complex salts.

The following examples illustrate the invention in more detail.

EXAMPLE 1

(a)

1-(p-Chloroanilino)-2-carbomethoxy-4-carboxybutadiene

Gentle heating is employed to dissolve 46.2 g of methyl coumarate in 30 ml of methanol and 38.1 g of p-chloroaniline in 60 ml of methanol. When the solutions have cooled down, they are slowly combined with stirring, and the mixture is cooled down. A precipitate of yellow crystals forms. The mixture is allowed to stand overnight, and the crystals are then filtered off with suction, are washed with methanol and are dried at 40° C. under 1.3 Pa over $P_2O_5$ in a desiccator. Yield: 76 g; melting point: 160°–161° C.

(b) Decarboxylation of (2) to 1-(p-chloroanilino)-2-carbomethoxybutadiene and subsequent Diels-Alder reaction with 1,4-anthraquinone to 2-carboxymethoxynaphthacene-5,12-quinone 14.05 g of compound (a) are dissolved in 60 ml of dimethyl sulfoxide, and the solution is stirred at room temperature overnight with evolution of $CO_2$. The result is a clear solution. 10.4 g of 1,4-anthraquinone are then dissolved in 500 ml of dimethylsulfoxide by heating to 50° C., the solution is combined with the clear solution, and the mixture is stirred at 80° C. for 24 hours. The result is a yellow crystalline precipitate. The reaction mixture is cooled down in an ice bath and is diluted with 250 ml of acetone, and the precipitate is filtered off with suction and is washed with ice-cold acetone. The result is 6 g of crude product. The mother liquors yield a further 2 g of crude product. The crude product is sublimed at 230° C. in a temperature gradient tube. The result is 7.7 g of pure 2-carboxymethoxynaphthacene-5,12-quinone (b) in a yield of 25%. Thin layer chromatogramme on silica gel with $CHCl_3$: a bright yellow fluorescent spot of $R_f=0.4$. IR bands at 1735 and 1690 cm$^{-1}$. Mass spectrum: $M^+=316$; M—$OCH_3=285$; 257 (285-CO); 229 (257-CO).

(c) Reduction of compound (b) to 2-carboxymethoxynaphthacene 7.7 g of compound (b), 23.1 g of Zn dust, 1150 ml of glacial acetic acid and, 62 ml of water are refluxed with stirring in a 2.5 liter sulfonating flask equipped with a stirrer and a reflux condenser. The mixture is then allowed to cool down and is decanted from excess Zn dust. The orange-red precipitate which is formed is filtered off with suction, is washed with a little glacial acetic acid and water and is dried in vacuo. The result is 3.9 g of crude product which is sublimed at 200° C. and 0.13 Pa in a gradient tube. The sublimate consists of 3.7 g (yield 53%) of pure 2-carbomethoxynaphthacene. The electron spectrum in benzene has $\lambda_{max}$=487, 457, 430, 404, 381 and 361 nm. Mass spectrum: $M^+$286, 255 ($M^+$—OCH); 227 (255-CO); 143 ($M^{2+}$).

(d) Preparation of 2-carbomethoxy-5,11-(or 6,12)-dichloronaphthacene 4 g of 2-carbomethoxynaphthacene are suspended in 50 ml of nitrobenzene under an argon blanket in a sulfonating flask, and the suspension is cooled in an ice bath. 4.05 g of sulfuryl chloride dissolved in 50 ml of nitrobenzene are slowly added dropwise in the course of 30 minutes. The ice bath is then removed, and the mixture is slowly heated to a bath temperature of 50° C. The mixture is stirred at this temperature for 1 hour and turns into a clear dark orange solution. When the solution has cooled down, 500 ml of methanol are added. The resulting reddish orange precipitate is filtered off with suction, is washed with cold methanol and is dried at 0.13 Pa and 50° C. The yield is 75%. Mass spectrum: $M^+$=354/356.

(e) 2-Carbomethoxy-5,6,11,12-tetrathiotetracene

In a sulfonating flask which is equipped with a stirrer, a reflux condenser and a gas inlet tube, 6.8 g of compound (d) and 2.6 g of sulfur in 200 ml of 1,2,4-trichlorobenzene are refluxed under an argon blanket for 8 hours. When the mixture has cooled down, the precipitated product is filtered off with suction and is recrystallised from boiling 1,2,4-trichlorobenzene. The result is fine, blackish green needles in a yield of 7 g (90%). Electron spectrum in trichlorobenzene: $\lambda_{max}$740 and 680 nm. Mass spectrum: $M^+$=410; M—COOCH$_3$=351.

EXAMPLE 2

2-Carbomethoxy-5,6,11,12-tetraselenotetracene

Example (1e) is repeated, except that selenium is used in place of sulfur. The reaction time is 120 hours. The isolated black solid is sublimed at 260° C. and 0.13 Pa in a temperature gradient tube. The yield is 5%. Mass spectrum: $M^+$=602. Visible spectrum in 1,2,4-trichlorobenzene: $\lambda_{max}$=754 and 694 nm.

EXAMPLE 3

Preparation of conductive CT salts of the type 2-carbomethoxy-5,6,11,12-tetrathiotetracene (SbFb)$_x$, and 2-carbomethoxy-5,6,11,12-tetrathiotetracene (Cl)$_x$ In each case 10 mg of 2-carbomethoxy-5,6,11,12-tetrathiotetracene are electrolysed in 30 ml of a mixture of 40% of methylene chloride and 60% of chlorobenzene and 30 g of tetrabutylammonium hexafluoroantimonate in one case and triphenylbenzylphosphonium chloride in the other in an electrolysis cell for 10 weeks at respectively 1.38 V/1.4×10$^{-7}$A and 0.93 V/4×10$^{-7}$A. The resulting microcrystals are contacted on glass plates at the ends with Pt paste and are tested for their resistance properties.

Conductivity (room temperature): ≃30 ohm$^{-1}$cm$^{-1}$ (SbF$_6$ salt)

Conductivity (room temperature): ≃0.2 ohm$^{-1}$cm$^{-1}$ (Cl salt)

EXAMPLE 4

6,-Hydroxyhexyl 5,6,11,12-tetrathiotetracene-2-carboxylate

A mixture of 1.2 g of 2-carbomethoxy-5,6,11,12-tetrathiotetracene, 30 g of hexanediol and 1 mg of tetraisopropyl titanate is heated with stirring under an N$_2$ blanket in a vessel to 150° C. and is left at said temperature for 20 hours. After the mixture has cooled down, 100 ml of water are added, and the reaction product precipitates. The product is filtered off, is washed with water and is dried at 100° C. in vacuo.

Elemental analysis: Calculated: C 60.46, H 4.06, O 9.66, S 25.82, Found: C 60.1, H 4.1, O 9.66, S 25.6.

EXAMPLE 5

Preparation of 2,3-dicarboethoxy-5,6,11,12-tetrathiotetracene (a) Diethyl α-pyrone-4,5-dicarboxylate A solution of 113.14 g (0.6 mole) of titanium tetrachloride in 150 ml of tetrachloromethane is added dropwise at 2°–3° C. to 1200 ml of tetrahydrofuran in the course of 40 minutes. An hour later and at the same temperature, 44.16 g (0.6 mole) of ethyl formate and 38.7 g (0.15 mole) of triethyl aconitate are added in succession. Finally, 120.93 g (1.2 mole) of N-methylmorpholine in 210 ml of tetrahydrofuran are added in the course of 45 minutes. After 15 minutes the mixture is poured with vigorous stirring into 1500 ml of H$_2$O, 200 g of sodium bicarbonate and 1400 ml of methylene chloride. The mixture is stirred until there is no further evolution of CO$_2$. The resultant suspension is filtered and the two phases of the filtrate are separated. The aqueous phase is extracted twice more with 300 ml of methylene chloride each time. The combined methylene chloride extracts are dried with sodium sulfate and are concentrated. The resulting crude product (44.95 g, 95.4%) yields on high vacuum distillation at 61° C. reacted components. The resulting distillation residue is 31.38 g (66.6%) of triethyl ethoxymethyleneaconitate. H$^1$-NMR spectrum: 6.85 (1H singlet), 7.5 (1H singlet). The product is processed further in its present state.

31.38 g (0.0999 mole) of triethyl ethoxymethyleneaconitate are heated at 95° C. in 314 ml of formic acid for 1 hour. The formic acid is distilled off under a water jet vacuum. High-vacuum distillation of the residue produces 10.00 g (62.4%) of diethyl α-pyrone-4,5-dicarboxylate (boiling point 82° C./1.2×10$^{-2}$ mbar). H$^1$NMR spectrum: 6.40 (1H singlet), 8.25 (1H singlet).

(b) Preparation of diethyl napthacene-5,12-quinone-2,3-dicarboxylate 15.97 g (0.076 mole) of 1,4-anthraquinone and 18.42 g (0.076 mole) of diethyl α-pyrone-4,5-dicarboxylate are heated at 160° C. in 34 ml of xylene in an autoclave for 24 hours. Xylene is distilled off, the distillation residue is dissolved in chloroform and is filtered through 1.2 kg of silica gel (particle size: 0.040–0.063 mm), and the silica gel is flushed with chloroform. The result is 16 g of crude dark brown substance which is subjected at 210° C. to a high-vacuum sublimation. Melting point: 208°–209° C.; mass spectrum: $M^+$=402.

(c) Preparation of diethyl tetracene-2,3-dicarboxylate 1.3 g of compound (b), 6.5 ml of H$_2$O, 110.5 ml of acetic acid and 6.5 g of zinc dust are combined, and the mixture is heated to the reflux temperature. The red suspension starts to turn orange. The suspension is stirred for 30 minutes and cooled down, and 130 ml of water are added. The excess zinc dust is decanted off from the residue, is washed with water and is dried at 40° C. under a high vacuum. The result is 860 mg of crude product which sublimes at 220° C. The crude product is a mixture of compounds (b) and (c) and diethyl 5,12-dihydrotetracene-2,3-dicarboxylate. The mixture is reduced once more with zinc dust.

500 mg of the then resulting crude product are refluxed for 2 minutes together with 500 mg of p-chloroanil in 15 ml of acetic acid. The mixture is allowed to cool down, and the orange precipitate is filtered off with suction and is dried under a high vacuum. High-vacuum sublimation at 190° C. produces 109 mg of compound (c) having a melting point of 224° C. Mass spectrum $M^+ = 372$.

(d) Preparation of diethyl 5,11-dichlorotetracene-2,3-dicarboxylate 109 mg of compound (c) and 2 ml of nitrobenzene are cooled in an ice bath and 90 mg of sulfonyl chloride in 2 ml of nitrobenzene are added dropwise. The ice bath is removed. A yellowish orange solution forms and is stirred at room temperature for 2 hours. It is then stirred at 90° C. for 1 hour. The orange solution is evaporated to dryness in a rotary evaporator. This produces 129 mg of compound (d). Mass spectrum $M^+ = 496$.

(e) Preparation of diethyl 5,6,11,12-tetrathiotetracene-2,3-dicarboxylate 129 mg of compound (d), 40 mg of sulfur and 3 ml of nitrobenzene are presented under argon in a pear-shaped flask, and the mixture is maintained at a bath temperature of 230° C. for 4 hours. When the mixture has cooled down, the nitrobenzene is removed under high vacuum, and the residue is washed with a little benzene and is dried. This produces 122 mg of the desired compound.

Mass spectrum: $M^+ = 496$; UV spectrum in 1,2,4-trichlorobenzene: $\lambda_{max} = 745$ nm.

EXAMPLE 6

Diethyl 5,6,11,12-tetraselenotetracene-2,3-dicarboxylate 120 mg of diethyl 5,11-dichlorotetracene-2,3-dicarboxylate, 120 mg of selenium and 6 ml of nitrobenzene are heated under argon for 21 hours (up to 260° C.). When the mixture has cooled down, 10 ml of hexane are added, and the precipitate is filtered off with suction. The result is 125 mg of crude product. 50 mg are sublimed at 260° C. under high vacuum. The result is dark green diethyl 5,6,11,12-tetraselenotetracene-2,3-dicarboxylate. Mass spectrum: $M^+ = 684$. UV spectrum in 1,2,4-trichlorobenzene: $\lambda_{max} = 756$ nm.

EXAMPLE 7

Preparation of an adduct on maleic anhydride/vinyl methyl ether copolymer 1 g of the hydroxy ester of Example 4 is dissolved in 20 ml of N-methylpyrrolidone, the solution is added to 0.35 g of Gantrez AN 119 ® (maleic anhydride/vinyl methyl ether copolymer), and the mixture is heated to 50° C. 0.3 ml of triethylamine is then added, and the mixture is stirred for 24 hours. The mixture is then poured onto 200 ml of water, and the precipitated product is filtered off, is washed with water and is dried at 60° C. under high vacuum.

Elemental analysis: Calculated: C 58.73; H 4.33; O 17.78; S 19.12; Found: C 58.4, H 4.2, O 15.1, S 21.6.

We claim:

1. 2-, or 2,3-substituted 5,6,11,12-tetrathiotetracene or -tetraselenotetracene of the formula I

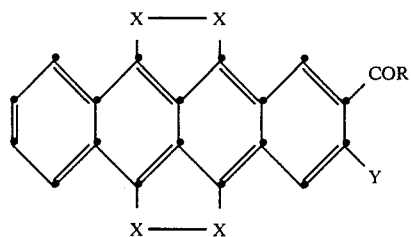

in which X is S or Se and R is alkoxy having 1 to 12 C atoms, cycloalkoxy having 5 to 16 C atoms, ω-hydroxyalkoxy having 2 to 12 C atoms, aryloxy having 6 to 16 C atoms, aralkoxy having 7 to 12 C atoms —OH, —NH₂, —Cl, —Br or —NR¹R² in which R¹ is alkyl having 1 to 12 C atoms, cycloalkyl having 5 to 16 C atoms, ω-hydroxyalkyl having 2 to 12 C atoms, aryl having 6 to 16 C atoms or aralkyl having 7 to 16 C atoms and R² is a hydrogen atom or independently is defined in the same way as R¹, and Y is a hydrogen atom or a —COR group or Y and R together are —CO—O— or —CO—NR².

2. Tetracene according to claim 1, in which R is alkoxy having 1 to 6 C atoms, ω-hydroxyalkoxy having 2 to 6 C atoms, —OH, —Cl, —NH₂ or NR¹R², in which R¹ is alkyl having 1 to 6 C atoms, ω-hydroxyalkoxy having 2 to 6 C atoms, phenyl or benzyl and R² is a hydrogen atom.

3. Tetracene according to claim 1, in which R is methoxy, ethoxy, 2-hydroxyethoxy, 3-hydroxypropoxy, 4-hydroxybutoxy, 6-hydroxyhexoxy, —OH, —Cl, —NH₂, —NHCH₃, —NHC₂H₅ or —NHCH₂CH₂OH.

* * * * *